United States Patent
Wiseman et al.

(10) Patent No.: US 6,500,777 B1
(45) Date of Patent: *Dec. 31, 2002

(54) BIORESORBABLE OXIDIZED CELLULOSE COMPOSITE MATERIAL FOR PREVENTION OF POSTSURGICAL ADHESIONS

(75) Inventors: David M. Wiseman, Dallas, TX (US); Lowell Saferstein, Edison; Stephen Wolf, Neshanic Station, both of NJ (US)

(73) Assignee: Ethicon, Inc., New Brunswick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/881,972

(22) Filed: Jun. 25, 1997

Related U.S. Application Data

(60) Provisional application No. 60/020,757, filed on Jun. 28, 1996.

(51) Int. Cl.[7] .............................................. B32B 27/12
(52) U.S. Cl. ...................... 442/286; 156/281; 156/336; 424/444; 442/304; 442/394; 604/304
(58) Field of Search ................................ 156/336, 281; 442/286, 304, 394, FOR 12; 424/444; 604/304

(56) References Cited

U.S. PATENT DOCUMENTS

| | | | | |
|---|---|---|---|---|
| 2,381,621 A | * | 8/1945 | Schmelkes et al. | ......... 604/304 |
| 3,328,259 A | * | 6/1967 | Anderson | .................... 604/304 |
| 5,134,229 A | * | 7/1992 | Saferstein et al. | .......... 424/444 |
| 5,447,940 A | | 9/1995 | Harvey et al. | |
| 5,789,465 A | | 8/1998 | Harvey et al. | |

FOREIGN PATENT DOCUMENTS

| | | |
|---|---|---|
| EP | 194 192 | 2/1986 |
| EP | 250 187 | 12/1987 |
| EP | 325 195 | 1/1989 |
| EP | 0 303 496 A | 2/1989 |
| EP | 0423155 B1 | 6/1989 |
| EP | 0 372 969 A | 6/1990 |
| EP | 567 234 | 10/1993 |
| EP | 97 30 4635 | 10/1999 |
| GB | 779 820 A | 7/1957 |
| WO | WO 90/13302 | 11/1990 |
| WO | WO 92/10218 | 6/1992 |

OTHER PUBLICATIONS

European Search Report Application Number EP 97 30 4635, Date of completion of the search Oct. 27, 1999 (not a reference).

* cited by examiner

Primary Examiner—John J. Gallagher

(57) ABSTRACT

An improved adhesion-preventative physical barrier, wound dressing and drug delivery system comprising an oxidized cellulose film made up of multiple layers of a cellulose fabric or like material and a cellulose film. A method for forming an improved oxidized cellulose film and for using the same to prevent the formation of postsurgical adhesions and/or to dress a wound and/or to deliver one or more drugs.

23 Claims, No Drawings

BIORESORBABLE OXIDIZED CELLULOSE COMPOSITE MATERIAL FOR PREVENTION OF POSTSURGICAL ADHESIONS

This application claims the benefit of U.S. Provisional Application No. 60/020,757 filed Jun. 28, 1996.

TECHNICAL FIELD

The present invention relates to physical barriers for the prevention of adhesions, and more specifically, to a bioresorbable oxidized cellulose composite material composed of oxidized cellulose film for prevention of post-surgical adhesions.

BACKGROUND OF THE INVENTION

Adhesions, or scar tissue bridges, are the abnormal connection of two or more body surfaces by fibrin associated with ingrowth of fibroblasts. Although the specific pathogenesis is not fully understood, such adhesions are likely produced as a result of the manipulative and chemical trauma associated with surgery. Such adhesions constitute a major source of postoperative morbidity and mortality. Indeed, up to ninety percent of all surgeries result in the formation of such adhesions and approximately ten percent of these adhesions result in serious complications for the patient. ELLIS, H., *The Causes and Prevention of Intestinal Adhesions*, BR. J. SURG. 69:241–43, 1982; WEIBEL M. A., MAJNO, G., *Peritoneal Adhesions and their Relation to Abdominal Surgery*, AM. J. SURG. 126:345–53, 1973. Such complications are location specific, but include infertility, intestinal obstruction, loss of range of motion in joints, and the like. For example, the formation of adhesions following cardiac surgery further increases the risks involved in a subsequent sternotomy. DOBELL A. R. C. AND JAIN, A. K., *Catastrophic Hemorrhage During Redo Sternotomy*, ANN. THORAC. SURG. 37: 273–78, 1984.

Potentially dangerous for patients and a nuisance for surgeons, adhesions have been the target of study for over a century. Previous attempts at prevention of adhesions can be classified as follows: (1) prevention of fibrin deposition; (2) removal of fibrin exudate; (3) inhibition of fibroblastic proliferation; and (4) separation of surfaces.

While each of these approaches have achieved a modicum of success, the use of physical barriers to limit tissue apposition during the healing period has yielded to date perhaps the most positive results. Wiseman, D. M., *Polymers for the Prevention of Surgical Adhesions*, in POLYMER SITE SPECIFIC PHARMACOTHERAPY, 369–421 (A. Domb ed. 1994)(John Wiley, Chichester, publisher). Early approaches to the use of physical barriers employed everything from fish bladder membranes to silver and gold foils. However, it was quickly realized that these attempts did not provide the prolonged effect necessary to prevent formation of adhesions. While more modern approaches have included the use of gels and liquids, the most promising approaches to date have utilized solid physical barriers.

One traditional approach to the use of a solid physical barrier includes the use of sheets of expanded polytetrafluoroethylene ("PTFE") to achieve the desired physical separation, as described in U.S. Pat. No. 5,468,505 to Hubbel et al. and by HANEY, A. F., HESLA, J., HURT, B., KETTLE, L. M., MURPHY, A. A., ROCK, J. A., ROWE G. & SCHLAFF, W. D., *Prevention of Pelvic Sidewall Adhesion Reformation Using Surgical Barriers: Expanded Polytetrafluoroethylene (Gore-Tex® Surgical Membrane) is superior to Oxidized Regenerated Cellulose (Interceed® TC7)*, FERTIL. STERIL. (Prog. Supp.), p. 265, s. 210 (1994). While providing the desired physical separation of the tissues, the PTFE is nonabsorbable and therefore is not preferred. The high potential for infection caused by foreign materials left in the body is well known in the art.

Attempts to utilize physical barriers made from absorbable materials, such as polylactide, polyglycolide and their copolymers have achieved limited success partly because the porosity and fibrous nature of the material exacerbates the natural defense mechanism of the body to foreign materials. WISEMAN, D. M. *Polymers for the Prevention of Surgical Adhesions* in POLYMER SITE SPECIFIC PHARMACOTHERAPY, 369–421 (A. Domb ed. 1994)(John Wiley, Chichester, publisher). Barriers such as that marketed by Johnson & Johnson under the trade name INTERCEED® (TC7) Absorbable Adhesion Barrier have been more successful because they are composed of oxidized regenerated cellulose ("ORC") which is less reactive with tissue. However even barriers composed of ORC described in U.S. Pat. No. 4,840,626 to Linsky, et al. have achieved only limited usage due in part to the fact that: (1) the material contains pores which do not close rapidly enough on hydration to prevent the penetration of fibrin from one side of the barrier to the other. It is this fibrin bridging from one tissue to another that initiates adhesion formation. The inventors of the composite material of the present invention have discovered that for some applications, such as for the prevention of pericardial adhesions, or in circumstances where there is prolonged fibrin deposition due to inflammation, a more substantial barrier with smaller pores is required for adhesion prevention; and (2) the barrier may lose its integrity or position too rapidly at certain anatomical sites (e.g. around the heart) where there is organ movement to facilitate disintegration and dislodgment.

It is known that materials composed of oxidized cellulose evoke a minimal tissue response. This was first discovered in 1936 by W. Kenyon at the Eastman Kodak Laboratories. During Mr. Kenyon's fundamental research on the oxidation of cellulose, it was discovered that a new type of product could be made by oxidizing cellulose using nitrogen dioxide. The new material was soluble in alkali and in contrast to the usual friable materials produced through other methods of oxidizing cellulose, the new material maintained its original form and much of its original tensile strength. It was shown that the new product was a copolymer of anhydroglucose and anhydroglucuronic acid. This new oxidized cellulose material was later developed into a bioabsorbable fabric hemostat by Parke Davis and Johnson & Johnson. A good discussion of the process can be found in the following references, all of which are incorporated herein by reference: Kenyon, R., *Oxidation of Cellulose*, INDUS.& ENGIN. CHEM., vol. 41 (1) 2–8, 1949; U.S Pat. Nos. 2,232,990, 2,298,387, 3,364,200 and 5,180,398 and its foreign equivalents, EP 0,492,990 and Japanese Application No. 361083/91.

Thus a need remains for a bioresorbable physical barrier for the prevention of postsurgical adhesions which is: (1) less porous than conventional woven or knitted fabric materials; (2) capable of being easily and securely attached to the desired location; and (3) does not contain pores which will permit deposition of fibrin and cellular ingrowth.

SUMMARY OF THE INVENTION

In accordance with one aspect of the present invention, a continuous composite film of oxidized cellulose is used as a physical barrier to limit tissue apposition, minimizing or preventing altogether the formation of postsurgical adhesions. The use of a continuous composite film overcomes the difficulties. The oxidized cellulose composite is constructed by forming a multi-layer sandwich of a cellulose film and an internal rip stop material, such as rayon, cellulose knitted, woven or non-woven fabric or cellulose paper. The films and fabric or paper are bonded together with a cellulosic adhesive such as starch, methylcellulose or oxidized with nitrogen dioxide which renders it bioabsorbable. Subsequently, it can be sterilized with gamma irradiation. This oxidation step converts the primary hydroxyl groups in the cellulose polymer to carboxyl groups and renders the polymer susceptible to aqueous and enzymatic hydrolysis.) The resulting material is then usefull for the preparation of surgically implanted, bioabsorbable medical products. The resulting oxidized cellulose multi-layered composite film has all of the desirable characteristics (e.g. bioresorbability, suturability, low tissue reactivity etc.) of a bioabsorbable fabric composed of oxidized cellulose along with the additional benefits of a smooth, lubricious, continuous non porous surface in contact with tissue. Because the composite film contains a rip-stop material, it may be sutured in place for example as a pericardial patch.

Additionally the adherence of cells and molecules will be reduced on the smooth film surface compared with that of a fabric surface due to the lower surface area available for absorption. This feature greatly improves the success rate of the physical barrier. Adhesion of cells to substrates strongly influences many of their functions and therefore plays an important role in a variety of biologic processes including growth, phagocytosis, hemostasis and the response of tissue to implanted materials. In a symposium on Surface Characterization of Biomaterials, sponsored by the American Chemical Society September 1986, Buddy Ratner and others showed that smooth surfaces of biomaterial implants evoke less cellular reaction and less tissue irritation than rough surfaces.

Moreover, the oxidized cellulose multi-layered film is flexible, durable and, most importantly, suturable. The flexibility of the material is improved by moistening with saline or other physiologically acceptable fluid just prior to use. Accordingly, the multi-layered film can be easily and securely attached (e.g. via suturing) to the desired location. The oxidized cellulose multi-layered film also lacks tackiness and therefore will not stick to gloves or surgical instruments.

In another aspect of the present invention, the oxidized cellulose film can be used without its combination with a rip-stop material. Since the oxidized cellulose film alone will tear if sutured, the oxidized cellulose film can be secured into position with a physiologically acceptable tissue adhesive such as fibrin glue or a cyanoacrylate based adhesive. The oxidized cellulose film alone will function as a suitable physical barrier, the smooth nature of the film reducing the adherence of cells and molecules to its surface.

In yet another aspect of the present invention, the oxidized cellulose composite film material can be combined with drug treatments, such as heparin, to increase the efficacy of the barrier. Such drugs may be bonded to the composite either by surface absorption or by soaking the composite in a solution of the drug after oxidation and before complete drying. In a related application, the oxidized cellulose composite film material can be used as a wound dressing. Due to its flexibility and drug absorption qualities, the oxidized cellulose composite material serves as a unique wound dressing. Additionally, such wound dressing can be used to deliver one or more drugs to a wound site to aid in the healing of such wound.

In its process aspects, the present invention includes a method for forming the oxidized cellulose composite film material of the present invention. Additionally, another process aspect of the present invention is the prevention of postsurgical adhesions through the positioning as a physical barrier, between the site of the surgery and the neighboring tissue, of the oxidized cellulose composite film material of the present invention to limit tissue apposition.

The use of the oxidized cellulose composite film multi-layered physical barrier of the present invention provides the physical barrier necessary to limit tissue apposition, the bioresorbability of an ORC material, as well as ease and security of attachment and reduced biosensitivity to the material.

In yet another aspect of the invention, the oxidized cellulose film is used as a wound dressing. And in yet a different aspect of the invention, the oxidized cellulose film used as a wound dressing also serves as a drug delivery device, delivering one or more drugs to the wound site to aid in healing the wound.

DETAILED DESCRIPTION

In the preferred embodiment of the present invention, an oxidized cellulose multi-layered film is positioned as a physical barrier, between the site of the surgery and the neighboring tissue, to limit tissue apposition and thus reduce the formation of postsurgical adhesions. The oxidized cellulose multi-layered film is formed according to the preferred embodiment of the present invention method for forming such oxidized cellulose multi-layered film. This film will consist of: (1) a fibrous cellulosic layer sandwiched in between (2) two sheets of cellulose film and glued together with (3) a glue of methylcellulose or starch paste. This composite material is then oxidized to produce the oxidized cellulose multi-layered film.

A methylcellulose glue is prepared by suspending approximately one gram of methylcellulose (degree of substitution 1.65 to 1.92) such as METHOCEL A4M™ brand methylcellulose from Dow Chemical Company in approximately 50 ml. of distilled water at approximately 140 F. The suspension is stirred while it is allowed to cool to room temperature. A clear, low viscosity solution of methylcellulose results.

Next, a cellulose film is dampened in distilled water and laid out flat on a glass plate or other smooth, flat and generally non-adhering surface. Appropriate cellulose films may be obtained from Flexel, Inc. of Covington, Ind. A small volume of methylcellulose solution previously prepared or starch paste is then smeared over the surface of the cellulose film. A fibrous cellulosic material, such as knitted or woven rayon fabric precursor used in the manufacture of Surgicel® or INTERCEED barrier™ from Johnson & Johnson, is then laid over the freshly glued surface of the cellulose film. A second cellulose film is lightly coated on one surface with the methylcellulose glue or starch paste and placed on the opposite side of the fabric to complete the sandwich. A sheet of non-adhering release paper is then placed on the composite and covered with a weight and allowed to dry for several days.

It is noted that although only two layers of the cellulose film and one layer of fibrous cellulosic material are described above, any number of layers of the cellulose film or fibrous cellulosic material, of any combination of fibrous cellulosic materials, can be used, if desired.

By way of illustration only and not limitation, in the present example a weight of 5 kg. was placed over the composite material, which was allowed to dry for a period of at least several days. Furthermore, although use of a weight and air drying are described herein, drying may be achieved by any combination of weight, time, temperature and air pressure using standard methods known to those skilled in the art, if desired. After drying, the multi-layered composite sandwich is weighed and placed into a resin kettle equipped with a sodium hydroxide trap vent. The vessel is flushed with nitrogen gas to displace air. Nitrogen dioxide is chilled to approximately 10 C and an amount equal to three times the weight of the composite material is placed in a small Erlenmeyer flask attached to the resin kettle through a side arm adapter. The nitrogen dioxide is allowed to warm to room temperature and to diffuse into the resin kettle containing the multi-layered composite. The multi-layered film is oxidized by exposure to one to four times its weight in nitrogen dioxide gas at a temperature of between approximately 20 C and 35 C. Preferably, the multi-layered film material is exposed to the nitrogen dioxide gas for a period of from between 4 and 48 hours at an ambient atmospheric pressure. Following exposure to the gas, the vessel is purged with pure nitrogen and the resulting oxidized cellulose multi-layered composite film is washed with a 90% isopropanol solution and air-dried.

The composite film may be plasticized by adding glycerol or the composite film may be plasticized by adding glycerol or propylene glycol(as a 10% solution) to the washing medium to impart flexibility.

Finally, the multi-layered film material is sealed in a package and sterilized via gamma irradiation (1.8 MRad). The resultant oxidized cellulose multi-layered composite film was found to dissolve completely in 0.5 N NaOH to give a water-thin solution. This indicates that the material is likely to be bioabsorbable. The carboxyl content of the oxidized cellulose multi-layered film was determined by titration to be from between 10% and 22% by weight. Since the maximum percent carboxyl content possible is 25.5%, this indicates that between 37% and 86% of the primary alcohol groups in the starting cellulose material has been converted to the carboxyl form.

Although the preferred embodiment described above utilizes a fibrous cellulosic fabric such as the rayon fabric used for the production of Surgicel® or INTERCEED Barrier™ oxidized fabric by Johnson & Johnson, it is noted that any other appropriate fibrous cellulose fabric or material could be used, if desired. Additionally, although methylcellulose glue is described above, any appropriate glues or adhesives capable of oxidation to produce a bioabsorbable material, such as starch, guar, dextran, ethylcellulose (degree of substitution 1.65 to 1.92), cellulose monoacetate (degree of substitution 0.3 to 1.0), carboxymethylcellulose (degree of substitution 0.38 to 1.45), hydroxyethylcellulose (commercially available as Natrosol, by Hercules), hydroxypropylmethylcellulose (degree of substitution 1.65 to 1.92), hydroxybutylmethylcellulose (degree of substitution 1.65 to 1.92) hydroxypropylcellulose (degree of substitution 1.65 to 1.92)or even Carboxymethylcellulose is available from Aqualon and is available in a variety of grades with degrees of substitution of 0.38 to 1.45. The commercially available ethyl cellulose polymer from Hercules has a DS of 2.46 which is too high to allow sufficient primary and secondary hydroxyl groups on the cellulose backbone to become oxidized, and to be rendered bioabsorbable, as evidenced by dissolution in 0.5N sodium hydroxide. However if ethyl cellulose with a degree of substitution of 0.3 to 1.0 is oxidized with nitrogen tetroxide, it will be transformed into a bioabsorbable oxidized cellulose derivative.

It is also noted that cellulose film is not the only material capable of use with the present invention. Other bioresorbable films, which are capable of oxidation to produce a bioabsorbable material, such as cellulose mono acetate films (degree of substitution 0.5 to 1.0), carboxymethylcellulose films (degree of substitution 0.38 to 1.45), ethylcellulose films (degree of substitution 0.3 to 1.0) and methylcellulose films (degree of substitution 1.65 to 1.92) also function as appropriate barriers to postsurgical adhesions when used in the present.

The relatively smooth nature of the surface of the oxidized cellulose multi-layered film, as compared with more porous and fibrous nature of traditional ORC materials, is believed to contribute to the advantageous lack of adherence by cells, macromolecules and other tissues.

TEST PROCEDURES USED

The efficacy of the various oxidized cellulose multi-layered films of the present invention can be determined by the rabbit pericardial adhesion and the rabbit sidewall adhesion models, as follows. All animals are assigned blindly and randomly to a treatment group which is revealed to the surgeon only upon completion of the abrasion.

Pericardial Adhesion Model

The model is performed as described in WISEMAN D. M., KAMP, L., LINSKY, C. B., JOCHEN, R. F., PANG, R. H. L., SCHOLZ, P. *Fibrinolytic Drugs Prevent Pericardial Adhesions in the Rabbit*. J. SURG. RES. 53; 362–68, 1992. Under anesthesia and aseptic technique, the thorax of a New Zealand white rabbit is entered via a midline sternal incision. The pericardium is similarly opened via incision and the anterior surface of the heart abraded using a piece of gauze wrapped around the forefinger of the surgeon. The anterior surface of the heart is stroked forty (40) times with the gauze in a controlled manner.

Next, if the bioresorbable adhesion barrier of the present method is used, an elliptical piece of the barrier material with axes of approximately 2"×1" is placed over the anterior surface of the heart and sutured to the pericardium, if desired. If the animal is a control animal, no physical adhesion barrier is used and the surgeon skips to the next step described below. The pericardium and thorax of the animal is subsequently closed in layers.

Twenty-three to thirty days following surgery, the animals are sacrificed and evaluated for postsurgical adhesions. The percentage adhesion involvement of a strip 1 cm in width and extending from the apex of the anterior cardiac surface to the base of the anterior cardiac surface is estimated. The strip represents the portion of the surface of the heart in intimate contact with the sternum, the region most likely to form adhesions and most likely to present difficulty to surgeons attempting to reenter the thorax.

The results obtained from the above-identified pericardial testing procedure, without the use of a drug solution, are shown in the following tables:

| | CONTROLS | |
|---|---|---|
| Treatment | Animal No. | Percent Adhesions |
| None | 228-50 | 100 |
| None | 228-30 | 70 |
| None | 228-05 | 100 |
| None | 229-04 | 90 |
| None | 229-19 | 100 |

-continued

CONTROLS

| Treatment | Animal No. | Percent Adhesions |
|---|---|---|
| Mean | | 92 |
| Standard Deviation | | 13.04 |
| N | | 5 |

OXIDIZED CELLULOSE MULTI-LAYER FILM

| Treatment | Animal No. | Percent Adhesions |
|---|---|---|
| Film | 225-14 | 15 |
| Film | 227-04 | 5 |
| Film | 228-31 | 30 |
| Film | 228-51 | 5 |
| Film | 228-40 | 60 |
| Film | 228-01 | 5 |
| Film | 229-14 | 25 |
| Film | 229-15 | 25 |
| Mean | | 21.25 |
| Standard Deviation | | 18.67 |
| N | | 8 |

As demonstrated by the treatment test results shown above, the animals treated with the oxidized cellulose multi-layered film adhesion barrier of the present invention exhibit a marked decrease in the formation of postsurgical adhesions (Student's T-test $p<0.001$). Furthermore, visual inspection of the cardiac surface revealed very little irritation caused by the oxidized cellulose multi-layered material.

Rabbit Sidewall Adhesion Model

The rabbit sidewall adhesion model is performed as described in DIAMOND, M. P., LINSKY, C. B., CUNNINGHAM, T., CONSTATINE B., DIZEREGA, G. S., DECHERNEY, A. H., *A Model for Sidewall Adhesions in the Rabbit: Reduction by an Absorbable Barrier*, MICROSURGERY 8; 197–200, 1987. Under appropriate anesthesia and aseptic technique and using female White New Zealand rabbits (2–6 kg.), the abdomen is entered via a low ventral midline incision. Using a number 10 scalpel blade and starting approximately 1 cm. from the uterine bifurcation, 2 cm. lengths on both sides of each uterine horn are scraped 20 times each. Hemostasis is achieved by tamponade. In addition, a full thickness (2×2 cm.) excision of the musculoperitoneal sidewall is made and the scraped uterine horn approximated to it using 6–0 suture, placed 3–5 mm from the edge of the traumatized sidewall and uterine horn. The wound is subsequently closed in layers. Two weeks following surgery, the animals are euthanized and the surgical area examined by a blinded observer to evaluate the formation of adhesions therein. The formation and nature of adhesions are evaluated according to a standard system in which the extent, type and tenacity of any adhesions are noted.

Although preferred embodiments of the invention have been described in the foregoing Detailed Description, it will be understood that the invention is not limited to the embodiments disclosed, but is capable of numerous rearrangements and modifications of parts and elements without departing from the spirit of the invention.

What is claimed is:

1. A method for forming an oxidized cellulose multi-layered bioresorbable film for use as an adhesion-preventative barrier, comprising the steps of:

spreading a cellulose film onto a surface;

combining at least one layer of a cellulose fabric material with said cellulose film with an adhesive material capable of oxidation to form a bioresorbable material to form a multi-layered film;

oxidizing the multi-layered film; and sterilizing the multi-layered film.

2. The method of claim 1, wherein the adhesive is selected from the group consisting of starch, guar, dextran, ethylcellulose, cellulose monoacetate, carboxymethylcellulose, hydroxyethylcellulose, hydroxypropylmethylcellulose, hydroxybutylmethylcellulose, hydroxypropylcellulose and microcrystalline cellulose.

3. The method of claim 1, wherein the cellulose film is selected from the group consisting of cellulose films, cellulose acetate films, carboxymethylcellulose films, guar films, konjac films, starch films, dextran films and methylcellulose films.

4. The method of claim 1, wherein oxidizing includes exposing the multi-layered film to nitrogen dioxide.

5. The method of claim 4, wherein the multi-layered film is exposed to nitrogen dioxide for between 4 and 48 hours.

6. The method of claim 4, wherein the multi-layered film is exposed to nitrogen dioxide under a pressure of between 1 and 5 atmospheres.

7. The method of claim 4, wherein the multi-layered film is exposed to nitrogen dioxide in a temperature of between 20° C. and 35° C.

8. The method of claim 1, further including the step of washing the multi-layered film after the oxidizing step and before the sterilizing step.

9. The method of claim 8, wherein the multi-layered film is washed with an isopropanol solution.

10. The method of claim 1, wherein sterilizing the multi-layered film employs gamma irradiation.

11. The oxidized cellulose multi-layered film produced by the method of claim 1.

12. The method of claim 1, further including the step of plasticizing the multi-layered film with at least one polyhydroxy alcohol to impart flexibility to the multi-layered film.

13. The method of claim 12, wherein the at least one polyhydroxy alcohol is selected from the group consisting of glycerol and propylene glycol.

14. The method of claim 1, wherein the step of combining at least one layer of a cellulose fabric material with said cellulose film to form a multi-layered film includes the use of a rip stop material.

15. A method for forming an oxidized cellulose multi-layered bioresorbable film for use as an adhesion-preventative barrier, comprising the steps of:

spreading a cellulose film onto a surface;

combining at least one layer of a cellulose fabric material with said cellulose film using an oxidizable carbohydrate adhesive material capable of oxidation to produce a bioresorbable material to form a multi-layered film;

oxidizing the multi-layered film in the presence of nitrogen dioxide for between 4 and 48 hours at a temperature of between 20° C. and 35° C. and a pressure of between 1 and 5 atmospheres; and sterilizing the multi-layered film.

16. The method of claim 15, wherein the cellulose film is selected from the group consisting of cellulose films, cellulose acetate films, starch films, guar films, konjac films, dextran films, carboxymethylcellulose films and methylcellulose films.

17. The method of claim 15, wherein the adhesive is selected from the group consisting of methylcellulose, carboxymethylcellulose, hydroxyethylcellulose, starch, guar, dextran, konjac and microcrystalline cellulose.

18. The method of claim 15, further including the step of washing the multi-layered film with an isopropanol solution after the oxidizing step and before the sterilizing step.

19. The method of claim 15, wherein sterilizing the multi-layered film employs irradiation.

20. The oxidized cellulose multi-layered film produced by the method of claim 15.

21. The method of claim 15, further including the step of plasticizing the multi-layered film with at least one polyhydroxy alcohol to impart flexibility to the multi-layered film.

22. The method of claim 21, wherein the at least one polyhydroxy alcohol is selected from the group consisting of glycerol and propylene glycol.

23. The method of claim 15, wherein the step of combining at least one layer of a cellulose fabric material with said cellulose film to form a multi-layered film includes the use of a rip stop material.

* * * * *